United States Patent [19]

Reddick

[11] Patent Number: 4,894,053
[45] Date of Patent: Jan. 16, 1990

[54] DOUCHE APPARATUS

[76] Inventor: David C. Reddick, 3866 Fairview, St. Louis, Mo. 63116

[21] Appl. No.: 236,723

[22] Filed: Aug. 26, 1988

[51] Int. Cl.$^4$ ............................................. A61M 3/00
[52] U.S. Cl. ..................................... 604/85; 604/113; 604/150; 604/279
[58] Field of Search .................................. 604/83–85, 604/149–150, 275, 279, 248, 113, 114

[56] References Cited

U.S. PATENT DOCUMENTS

| | | | |
|---|---|---|---|
| 697,412 | 4/1902 | McMurran | 604/279 |
| 1,606,366 | 11/1926 | Hillman | 604/83 |
| 2,117,622 | 5/1938 | Morton et al. | 604/279 |
| 2,272,381 | 2/1942 | Marvin | 604/113 X |
| 2,829,645 | 4/1958 | Matteson | 604/150 |
| 3,044,465 | 7/1962 | Anderson et al. | 604/150 X |
| 3,104,664 | 9/1963 | Ladd | 604/150 |
| 3,769,976 | 11/1973 | Victory | 604/150 |
| 4,386,928 | 6/1983 | Hart | 604/83 |

*Primary Examiner*—Dalton L. Truluck

[57] ABSTRACT

A douche apparatus for vaginal application with a high temperature thermostatic valve located close to the source of mixed hot and cold water immediately after an adapter for connecting the apparatus to the water faucet. The apparatus has a hollow handle with a threaded extension which receives a disposable nozzle for vaginal introduction of douche liquids received through the handle. A flexible hose connects the thermostat output to a backflow prevention valve at the handle input to prevent douche additives introduced through a mixing chamber in the handle from being introduced to the water supply. A gate valve in the handle controls liquid volume and pressure in the flow channel exiting the handle through a macro screen for particulate matter filtration and a micro screen for bacterial filtration of the douche liquid immediately prior to exiting the handle and communication to the nozzle for vaginal cavity entry. The nozzle has downwardly curving channels extending from its hollow interior to its surface orifices to provide indirect douche liquid contact with vaginal surfaces. The handle end of the nozzle has a conically flared collar sloping outward and away from the nozzle to deflect douche liquid emerging from vaginal cavity from the handle and the user.

4 Claims, 1 Drawing Sheet

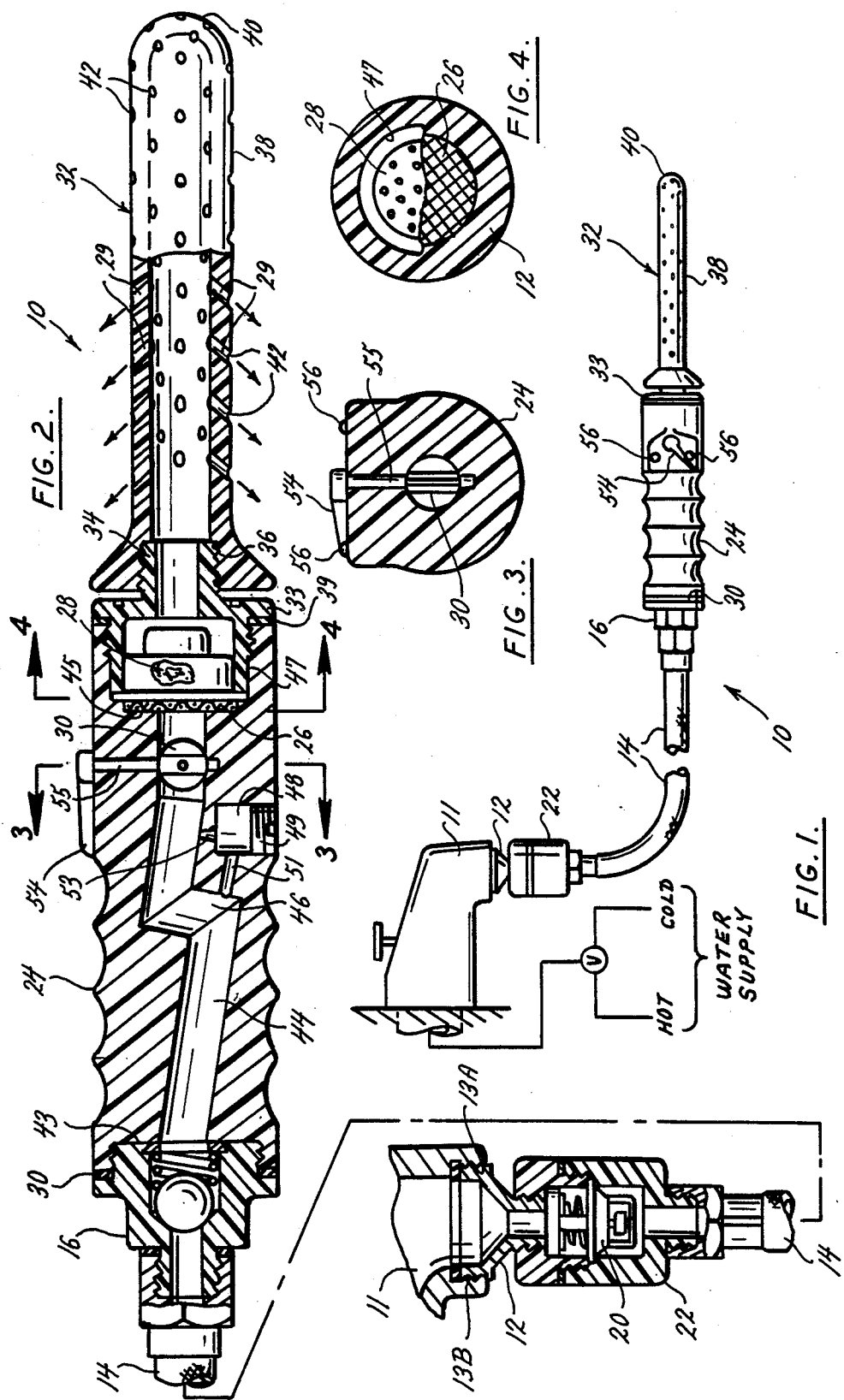

DOUCHE APPARATUS

BACKGROUND OF THE INVENTION

The present invention relates to vaginal cleansing and in particular is a vaginal douche apparatus.

Vaginal hygiene and the medical treatment of vaginal irritations and other feminine hygiene problems are applications for which a number and variety of types of vaginal douche devices have been developed. Douche devices that have been developed and are in some measure of use vary from the simple gravity feed and hand held syringe to the more complicated and sophisticated versions which include various types of valving and grooves for introducing medicines and cleaning agents required for particular medical and hygenic conditions. Whether simple or complex, all of these devices have a number of problems in common. One such problem is the fact that when water is used either by itself or in combination with an additive for medicinal or cleansing purposes, the liquid retained within the device after use can leave contaminants in the interior of the device which must be removed by back washing or flushing. If the back washing or flushing is not done properly, bacterial contamination and other types of contamination such as particulate matter including minerals and seals may be retained in the douche apparatus. During subsequent use, contaminants may cause irritation and actually create problems for which the device is being used medically and hygenically in the first place. Another type of problem relating to these devices is the problem associated with providing the desired and correct amount of water or other liquid pressure for introduction of the douche fluid into the vagina. It is, of course, necessary for the liquid to be able to be introduced into the vagina in such a way that it can perform the required cleansing, and treatment functions for which it is intended. The liquid flow must be introduced in such a way that it accomplishes its intended purpose without causing injury to the vaginal tissue. Thus, many of the douche devices in the prior art have provided for pressure control and pressure release so that excessive liquid flows are not introduced into the vagina. Another issue that has not been addressed in the prior art is that relating to the temperature of water being used in the vaginal douche device. It is obviously just as important that water temperature control be maintained, as it is that pressure control be maintained, in order not to cause injury or damage to the user. Reference is occasionally seen to the need for providing the appropriate mix of hot and cold water to the douche device. The assumption is apparently always made that the user will set the correct water mix so that the liquid entering the douche apparatus is a comfortable and correct temperature. The issue that arises of course is that the temperature of the water being provided from the source, usually a bathtub or shower head, can be set initially but cannot necessarily be relied upon to remain at the desired temperature. As an example, someone else living at or residing in the facility where the douche apparatus is being used may turn on a cold water tap elsewhere in the facility and result in a drop in the cold water pressure being mixed with hot water entering the douche apparatus. If a drop out of cold water into the mix is sudden the hot water component of the mix may increase suddenly with the result that a much higher temperature water flow will be entering into the douche apparatus, and if the apparatus is already inserted into the vagina the high temperature water will be introduced directly without adequate much opportunity for the user to remove the device before the hot water causes injury or damage to the vaginal tissue.

Another issue of significant concern that needs to be addressed when one is considering the use of a vaginal douche device is the safety of the water supply being used for introduction of the douche liquid. It is well known in clinical laboratory circles that the bacterial loading of water supplies in various geographical areas varies from season to season. In particular, it is well known that during the summer months many water supplies in metropolitan areas carry a much heavier bacterial loading then they do at other times of the year. The types of bacteria vary considerably also. In addition to bacteria of course there are other contaminants in the water supplies. These vary from mineral contaminants which may or may not cause problems to a particular individual depending upon their alergic sensitivities, to outright pollutants that remain in the water supplies even after extensive treatment. The issue of bacterial and other particular types of contaminants being introduced through the douche device from the water supply has not been addressed to any measurable degree in the devices of the prior art.

Another area of concern in providing a safe and effective douche device which will be useful in providing hygienic and medical treatment to the vagina without causing injury to it, is the manner in which the douche liquid is introduced within the vagina and its effect on the vaginal tissue. In most of the devices of the prior art the fluid introduction is directly against the vaginal tissue. In some medical conditions where the vaginal tissue has become irritated it is more appropriate to have a diffused liquid introduction which does not directly impact upon that tissue and cause additional irritation.

SUMMARY OF THE INVENTION

It is thus an object of the present invention to provide a douche apparatus which can be readily adapted to the most commonly found faucets associated with combination hot and cold water supplies.

It is another object of the present invention to provide a douche apparatus which can use a continuous flow of douche liquid and control that liquid as it is introduced into a vaginal cavity.

It is another object of the present invention to introduce the douche liquid through the device into the vaginal cavity so that it is diffused and indirect and does not impinge in a harsh manner upon the vaginal wall tissue.

It is another object of the present invention to provide back-flow prevention so that the water supply source to the device is not contaminated by the douche medication or any douche additive being used.

It is another object of the present invention to provide a douche additive capability.

It is yet another object of the present invention to provide a douche apparatus which employs a disposable plastic end piece which is the means for introduction of the douche liquid from the device into the vaginal cavity.

It is yet another object of the present invention to provide multi-stage filtering to eliminate or minimize the amount of particulate matter and bacteria being carried by the water from the supply source from getting through the douche apparatus and entering into the vaginal cavity of the user.

It is yet another object of the present device to provide a means for maintaining water pressure and flow control through the device.

Finally, it is an object of the present invention to provide a means of thermostatic control within the douche apparatus of the present invention so that any change in the hot water component entering the douche apparatus can be detected and shut off immediately so that no burn injury is caused to the user.

The present invention uses an adapater which fits into the single faucet type of water supply found in most bathtub arrangements in use today. The single faucet supply permits the mixing of hot and cold water entering into the faucet so that either hot or cold or a mix of both is discharged from the single faucet. The present invention then provides a thermostatic valve immediately adjacent to the water supply source to the douche apparatus so that if a sudden high temperature change in the water temperature leaving the faucet is detected, the thermostatic valve will shut off the supply of water. The intent here is, of course, to stop hot water entering into the device before it has any chance at all of getting discharged into the vaginal cavity where it can cause injury. A flexible hose leads from the thermostat housing to a back-flow prevention valve which is attached to the entry of the handle for the douche apparatus of the present invention. A back-flow prevention valve is intented to cut off any back-flow of douche liquid from the apparatus of the present invention so that douche additives that may have been added using the device cannot get back into the water supply serving the device. A flow channel having a double 90 degree transition intermediate between its two ends, leads between the back-flow prevention valve and a receptacle at the discharge end of the handle of the apparatus. As the flow channel makes its first 90 degree turn in the transition section within the handle a small bleed channel leaves the main flow channel and enters into an additive chamber which lies between the flow channel and the surface of the handle. The additive chamber has a cap to close it off during use. The cap is threaded into the additive chamber from the surface of the handle and when completely inserted is flush with the suface of the handle. A second bleed channel leaves the additive chamber and connects to the main flow channel after it has made its second 90 degree turn and is continuing in its original direction through the handle. Thus, water from the supply entering the douche apparatus through the flow channel bleeds off through the first bleed channel entering into the additive chamber in which a medical or hygenic type of douche additive may have been introduced, and the liquid or dissolved solid additive picked up and carried by the liquid moving through the additive chamber leaves through the second bleed channel and is introduced to the flow channel where the bleed channel connects with it downstream from the transition area. Downstream of the additive chamber in the flow channel, a gate valve is located within the flow channel in order to control the flow and pressure of the water or douche liquid moving through the douche apparatus. The gate valve is attached to a stem which extends transversly through the handle to a valve handle on the surface of the handle. The extent of control of the gate valve is related to the degree to which the valve handle can turn the gate valve between two stops separated from each other on the surface of the handle.

Further downstream a micro screen for filtering out particulate matter that may exist in the water supply is located immediately before a micro screen which is disposed within the flow channel in order to remove bacteria which also may exist within the water supply feeding the douche apparatus. The micro screen is located as far downstream within the flow channel in the handle as possible to make sure that any bacteria in the device whether picked up in the water supply or otherwise existing within the douche apparatus handle is successfully removed before the douche liquid exits the apparatus handle and enters into the disposable nozzle. The macro and micro screens are located within a receptacle at the end of the handle. The end of the handle immediately prior to the nozzle of the apparatus is closed off with an end cap which has a threaded male extension to which the female threading internal to the flared collar end of the nozzle is connected. The nozzle of the douche apparatus is a disposable element in the shape of a long finger with a flared base which threads onto the male threads of the end cap of the handle. This is effected by means of the female threads within the flared base of the disposable nozzle. A semi spherical tip is located at the other end of the nozzle. The entire nozzle has a hollow cylindrical interior which feeds douche liquid coming into the nozzle through nozzle channels which are angled and curved downward in a direction away from the semi spherical tip of the nozzle to orifices which direct the douche liquid down and around the surface of the vagina about the outer surface of the nozzle. Thus, not only does the douche apparatus of the present invention control the pressure and flow rate of the liquid coming through the apparatus and exiting through the disposable nozzle into the vagina, but the exit from the nozzle of the device occurs in such a way that a gentle flushing action occurs rather then direct impingment of the douche liquid upon the walls of the vagina. In addition, liquid or soluable solid douche additives are easily added in an uncomplicated manner within the handle of the device. Further, immediately adjacent to the entry of the device after the adapter to the water source, a thermostatic valve is used to cut off any excessively high temperature water which may suddenly be introduced to the device as a result of cold water in the mixing portion of the source becoming unavailable or for any reason when high temperature water suddenly begins to enter the apparatus. The thermostat is intended to gradually begin to close as the water temperature rises and then to immediately shut off when the water temperature reaches a certain level which is deemed potentially injurious if the water traverses the entire device and enters into the vagina. Finally, at the end of the handle used in the present apparatus a combination of filters is used to remove both particulate and bacteriological matter in the water leaving the device and entering the nozzle for disposition within the vagina. The bacteria filter is the last of the two filtering devices in the handle to insure that not only bacteria from the water supply but any bacteria in the system prior to the disposable nozzle are eliminated. The device is easily producible and, as will be seen in the discussion and drawings included hereinafter, is easily disassembled and cleaned. Drying upon completion of a cleaning procedure is also easily accomplished.

BRIEF DESCRIPTION OF THE DRAWINGS

The present invention will be more clearly understood as the description provided within the following drawings is examined and followed in the course of the discussion of the narrative disclosure herein. The drawings include:

FIG. 1 is a general pictorial of the entire present invention as it is connected for use with a mixing faucet.

FIG. 2 is a side cross sectional view of the invention.

FIG. 3 is a sectional view through the apparatus taken along line 3—3 in FIG. 2.

FIG. 4 is a multi-level sectional view taken through the douche apparatus of the present invention along line 4—4 in FIG. 2.

DESCRIPTION OF THE PREFERRED EMBODIMENT

Referring to FIG. 1 the douche apparatus is shown fully assembled and connected for use. Thus, as seen in both FIGS. 1 and 2, the douche apparatus is attached to the faucet 11 by means of an adapter 12 which has female threads 13a shown in FIG. 2 engaging the female threads 13b of the mixing faucet 11. A sensitive hot water thermostat 20 is incorporated within the thermostat housing 22 which is next and immediately connected to the outlet of the adapter 12. The output side of the thermostat housing 22 is connected to a braided flexible hose 14 which then mates with the back-flow prevention valve 16 threaded into the first female receptacle 43, in contact with the seal 30. The first female receptacle 43 is at the entry end of the handle 24 of the apparatus 10. The flow channel 44 connects the first female receptacle 43 at the entry end of the handle 24 to the second female receptacle 47 at the exit end of the handle 24. At an intermediate point within the flow channel 44 the double 90 degree transverse transition 46 occurs. At the first 90 degree turn an entry bleed channel 51 extends from the transverse wall of the flow channel 44 into the additive chamber 48. The additive chamber 48 is located intermediate between the continuing segment of the flow channel 44, after the transition 46, and the surface of the handle 24. The threaded cap 49 which is flush with the surface of the handle 24 is used to close off the additive chamber 48 when the douche apparatus 10 is in use. The exit bleed channel 53 extends from the bottom of the additive chamber 48 and connects into the continuing segment of the flow channel 44 prior to its emergence from the handle 24 by way of the second female receptacle 47. Downstream in the flow channel 44 from the additive chamber 48, the gate valve 30 is disposed and connected to the stem 55 which in turn connects to the valve handle 54 on the surface of the handle 24. The valve handle 54 is constrained to move between two stops 56 as seen in FIG. 1, and one of which is seen in FIG. 3, so that the gate valve 30 can be turned to close off the flow channel 44 entirely or to open the flow channel to varying degrees to control the amount of flow through the douche apparatus and the pressure of the water or douche liquid emerging from it. Finally, within the second female receptacle 47 at the end of the flow channel 44, the macro screen receptacle 45 is shown containing the macro screen 26 for removing particulate matter from the douche liquid moving through the douche apparatus 10. A final filter downstream from the macro screen is the micro screen 28 which is included to remove bacteria which may have entered the douche apparatus 10 from the water supply or to have been picked up during the transit of the douche liquid through the douche apparatus 10. The macro screen 45 and the micro screen 28 are retained within the second female receptacle 47 by means of the handle end cap 33 which has male threads threadably inserted into the second female receptacle 47 and engaging the female threads therein. The handle end cap 33 is threaded into the second female receptacle 47 until it is fully seated therein upon the seal 39. The flow channel 44 extends from within the second female receptacle 47 through a male extension 34 which is structurally a part of the handle end cap 33.

The nozzle 32 which is used for vaginal introduction of douche liquid provided through the flow channel 44 in the handle 24 of the douche apparatus 10 is a finger like tubular shaped device which has a hollow interior. The hollow interior of nozzle 32 becomes an extension of the flow channel 44 when the nozzle 32 is threadably introduced by means of the threaded female fitting 36 upon the threaded male extension 34 of the handle end cap 33. The nozzle 32 has a semi spherical tip 40 and the entire nozzle 32 contains a series of nozzle channels 29 which curve around and down from the interior flow channel 44 within the nozzle 32 to orifices 40 on the surface of the nozzle 32. The disposable nozzle 32 is fabricated from a biologically and chemically inert moldable material.

The gate valve 30 is seen in its fully open position within the flow channel 44 in FIG. 3. The macro screen 26 for filtration removal of particulate matter from the water or douche liquid traveling through the douche apparatus 10, and the micro screen 28 for removal of bacteria in the douche liquid before it exits the handle 24 of the douche apparatus 10 and enters the nozzle 32 on its way into the user's vagina, are shown in the partial cross sectional view of the handle in FIG. 4.

Thus, as operationally seen in FIGS. 1 and 2 once the adapter 12 is inserted into the mixing faucet 11 which is connected to the hot and cold water supplies, the douche apparatus 10 receives a mixture of hot and cold water through the thermostat 20 within the thermostat housing 22 unless the water temperature increases substantially, as might be the case where the cold water supply where to be suddenly cut off. In such a case the thermostat 20 which is located immediately adjacent to the faucet 11 will cut off the supply of the excessively hot water, long before it has a chance to traverse the douche apparatus 10 and enter the user's vagina. A flexible hose 14, which may be of the braided variety, extends from the thermostat housing 22 to the back-flow prevention valve 16 which is seated upon the seal 30 within the first female receptacle 43 at the entry end of the handle 24. The back-flow prevention valve 16 keeps any douche liquid within the douche apparatus 10 from traveling backward out of the douche apparatus 10 and into the water supply via the faucet 11. The additive chamber 48 is positioned within the flow channel 44 at the transition 46 in such a way that it receives water entering the handle 24, permits dilution of an additive which may have been included within the chamber 48 and passes the mixture out through the exit bleed channel 53 into the main flow chamber 44. The gate valve 30 is used to adjust the flow and pressure of the douche liquid leaving the handle 24 by way of the second female receptacle 47 through a series of two filters. The first filter is the macro screen 26 located within the macro screen receptacle 45 at the entry to the second female receptacle 47 and the second filter is the micro screen 28 which follows the macro screen in the second female receptacle 47. The micro screen 28 is selected to filter out any bacteria which may be introduced into the douche apparatus 10 either from the water supply, the additives, or from any source of bacterial contamination which may have continued to exist within the handle 24 after the previous cleaning. The material for use as the micro screen 28 is Nalgene 0.45 micron nitrocellulose disposable filter material manufactured by Nalge Company, a subsidiary of Cuibron Corporation of Rochester, N.Y., U.S.A. As can be seen in FIG. 2, the micro screen 28 is the last filter physically located within the structure of the handle 24 before any douche liquid leaves the handle 24 and is introduced into the nozzle 32 for discharge into the user's vagina. The filters are retained within the second female receptacle 47 by means of the handle end cap 33 which is threadably introduced into the second female receptacle 47 by means of the end cap male threads 35. As the handle end cap 33 is threaded into the second female receptacle 47 it seats upon the rubber-like seal 39 which keeps the douche liquid moving through the handle 24 from escaping. The disposable rigid or semi-rigid molded plastic or rubber-like nozzle 32 having the female fitting 36 within its conical flared collar 37 is threadably turned upon the threaded male extension 34 of the handle end cap 33. The nozzle 32, which is fabricated from chemically and biologically inert material, provides a gently flushing action by means of the curved and downward directed nozzle channels 29 from the hollow interior of the nozzle 32 which is an extension of the flow channel 44 from the handle 24, to the surface orifices 42 of the nozzle 32. The orifices 42 are located in a predetermined pattern upon the surface of and about the nozzle 32 along its entire length and upon its semi-spherical tip 40.

It should be obvious to those skilled in the art that the sizes and characteristics of many of the features of the present invention can be varied within the limits of the claims that I make for my invention without exceeding the bounds of those claims. Thus, the size of the nozzle 32 may be changed in diameter and length and the size of the handle 24 may likewise be changed. Further, the materials selected for the handle 24 and the nozzle 32 can be changed to vary rigidity and inertness to interaction with liquids being used. What I now claim as my invention is:

I claim:

1. A douche apparatus, comprising:
    a. means for adapting said apparatus to a source of combined hot and cold water from individual supplies that permit adjustment of flow and mix for volume and temperature setting,
    b. a nearly cylindrical handle having a first threaded female receptacle at one end, and second female threaded receptacle at its opposite end, and a hollow, liquid, axial flow channel between said female receptacles, said flow channel having a transverse transition at a location intermediate the opposing ends of said handle,
    c. means connected between said adapting means and said first threaded female receptacle of said handle for communicating water from said source,
    d. an additive chamber radially disposed between the outer surface of said handle and said flow channel at a point downstream from said transition, said chamber having a fluid input connection from said transverse transition and a fluid return connection to said axial flow channel after said transition, said additive chamber having a female threaded entry and a cap with corresponding male threads for positive closure,
    e. a gate valve rotatably disposed in said axial flow channel between said fluid return and said second female receptacle said gate valve connected to a rotatable stem transversely exiting said handle to an attached valve handle rotatably operable upon the surface of said douche apparatus handle between two stops located thereon, said stops corresponding to the fully closed and open conditions of said gate valve in said flow channel,
    f. a macro screen receptacle between the terminus of said flow channel and said second female receptacle,
    g. a micro screen within said second female receptacle abutting said macro screen,
    h. a handle end cap threaded into said second female receptacle,
    i. a cylindrically-shaped tube having a hollow central portion and an open end with one side of a mating connector for connection to the exit of said nearly cylindrical handle, said cylindrically-shaped tube having a plurality of holes spiralling radially downward and around said tube toward its open end, from said hollow, central portion to its exterior, and a semi-spherically-shaped tip at its opposite end, said tip having a hollow central portion connecting with the hollow central portion of said cylindrically-shaped tube, and a plurality of holes directed radially downward and around said tip towards said holding means, from said hollow, central portion of said tip to its exterior,
    j. a thermostaticaly controlled valve connected between said adapting means and said communicating means, and
    k. a back-flow prevention valve connected between said adaptive means and said nearly cylindrical handle.

2. The douche apparatus of claim 1 wherein said cylindrically shaped tube is fabricated from a semi-rigid, biologically and chemically inert material.

3. A douche apparatus, for use with a single faucet water fixture providing a source of water combined from apparatus separate sources of hot and cold water, said apparatus, comprising:
    (a) an adapter for connecting said apparatus to said faucet,
    (b) a cylindrically-shaped tube, for douche introduction into a body cavity, said tube having one end closed by a hemispherical cap containing a plurality of openings, a plurality of passages curving radially out and downward from its hollow interior to openings on its surface, and having an opposite end open and having one side of a mating connection,
    (c) a near cylindrically shaped apparatus handle having an entry end and an exit end and a flow-through central portion there-between, and having one-half of a mating connector at each of said ends, the connector at said exit end mating with the connector at the open end of said cylindrical tube for douche introduction, said apparatus handle further having a gate valve for pressure control disposed rotatably in said flow-through central portion and connected by means of a rotatable stem to a valve handle on the outside of said apparatus handle, said handle having two stops located adjacent to said valve handle to limit its rotation so as to constrain the operation of said gate valve between fully closed and partially open, said apparatus handle further having a port closed by a movable cover, said port being located on the body of said apparatus handle between the position of said gate valve and the exit end of said apparatus handle to accommodate douche additives, said apparatus handle additionally containing a filter receptacle at its entry end, said receptacle having an inner position and an outer position, (d) a micro filter for bacteria elimination from the flow through channel within said apparatus handle, said micro filter being located in the inner position of said filter receptacle, (e) a macro filter for rust, scale, and other particulate matter elimination from the flow through channel within said apparatus handle, said macro filter being located in the outer position of said filter receptacle, (f) a back-flow valve having and entry end and an exit end, each of which has a mating half of a connector, the exit end of said valve being connected to the entry end connector of said apparatus handle, (g) a thermostat having an entry end and an exit end, each of which has one side of a mating connector, the entry end connector being secured to the exit connector of said adapter, and (h) a flexible hose having two ends, each with one side of a mating connector, one end of which mates with and connects to the exit connector of said adapter, and the other end of which mates with and connects to the entry to said backflush valve.

4. The douche apparatus of claim 3 wherein said cylindrical tube further comprises a conically flared collar sloping downwardly and outwardly from the surface of said tube near its open end to a maximum flare away from and at the open end of said tube.

* * * * *